United States Patent
Penny

(10) Patent No.: US 11,607,283 B2
(45) Date of Patent: Mar. 21, 2023

(54) DYNAMIC CONTROL OF SURGICAL INSTRUMENTS IN A SURGICAL SYSTEM USING REPULSION/ATTRACTION MODES

(71) Applicant: Asensus Surgical US, Inc., Durham, NC (US)

(72) Inventor: Matthew Robert Penny, Holly Springs, NC (US)

(73) Assignee: Asensus Surgical US, Inc., Durham, NC (US)

( * ) Notice: Subject to any disclaimer, the term of this patent is extended or adjusted under 35 U.S.C. 154(b) by 420 days.

(21) Appl. No.: 16/733,154

(22) Filed: Jan. 2, 2020

(65) Prior Publication Data

US 2020/0205919 A1    Jul. 2, 2020

Related U.S. Application Data

(60) Provisional application No. 62/787,339, filed on Jan. 1, 2019.

(51) Int. Cl.
| | | |
|---|---|---|
| *A61B 34/30* | (2016.01) | |
| *A61B 34/37* | (2016.01) | |
| *A61B 34/00* | (2016.01) | |
| *B25J 9/16* | (2006.01) | |

(52) U.S. Cl.
CPC .............. *A61B 34/37* (2016.02); *A61B 34/25* (2016.02); *A61B 34/76* (2016.02); *B25J 9/1682* (2013.01)

(58) Field of Classification Search
USPC ............................... 700/245–264; 606/1, 130
See application file for complete search history.

(56) References Cited

U.S. PATENT DOCUMENTS

| | | | | |
|---|---|---|---|---|
| 7,153,297 B2* | 12/2006 | Peterson | ................. | A61B 90/36 606/1 |
| 8,620,473 B2* | 12/2013 | Diolaiti | ................... | A61B 34/37 600/407 |
| 9,737,371 B2* | 8/2017 | Romo | ..................... | A61B 34/30 |
| 9,974,613 B2* | 5/2018 | Kang | ................. | A61B 17/1622 |
| 10,130,429 B1* | 11/2018 | Weir | ....................... | A61B 34/76 |
| 11,234,781 B2* | 2/2022 | Penny | ..................... | A61B 34/20 |
| 2004/0106916 A1* | 6/2004 | Quaid | .................... | A61B 34/71 606/1 |
| 2013/0096574 A1* | 4/2013 | Kang | ..................... | A61B 34/37 606/130 |
| 2016/0270867 A1* | 9/2016 | Scholan | ................. | A61B 34/70 |
| 2017/0151021 A1* | 6/2017 | Quaid, III | .......... | A61B 17/1703 |
| 2017/0189127 A1* | 7/2017 | Weir | ....................... | A61B 34/20 |
| 2017/0340396 A1* | 11/2017 | Romo | .................... | B25J 9/1694 |
| 2018/0280110 A1* | 10/2018 | Meglan | .............. | A61B 1/00006 |
| 2020/0397520 A1* | 12/2020 | Penny | ..................... | A61B 34/25 |

* cited by examiner

*Primary Examiner* — Jonathan L Sample

(57) ABSTRACT

A robot-assisted surgical system has a user interface operable by a user, a first robotic manipulator having a first surgical instrument, and a second robotic manipulator having a second surgical instrument. The system receives user input in response to movement of the input device by a user and causes the manipulator to move the first surgical instrument in response to the user input, determines a vector defined by the position of the first surgical instrument relative to the second surgical instrument, generates dynamic control signals based on the determined vector, and causes the manipulator to move the second surgical instrument in response to said dynamic control signals.

15 Claims, 2 Drawing Sheets

DYNAMIC CONTROL OF SURGICAL INSTRUMENTS IN A SURGICAL SYSTEM USING REPULSION/ATTRACTION MODES

BACKGROUND

There are various types of surgical robotic systems on the market or under development. Some surgical robotic systems use a plurality of robotic arms. Each arm carries a surgical instrument, or the camera used to capture images from within the body for display on a monitor. Other surgical robotic systems use a single arm that carries a plurality of instruments and a camera that extend into the body via a single incision. Each of these types of robotic systems uses motors to position and/or orient the camera and instruments and to, where applicable, actuate the instruments. Typical configurations allow two or three instruments and the camera to be supported and manipulated by the system. Input to the system is generated based on input from a surgeon positioned at a master console, typically using input devices such as input handles and a foot pedal. Motion and actuation of the surgical instruments and the camera is controlled based on the user input. The image captured by the camera is shown on a display at the surgeon console. The console may be located patient-side, within the sterile field, or outside of the sterile field.

The Senhance Surgical System marketed by TransEnterix, Inc. is a robotic system allowing surgeon control of the robotic manipulator that supports the camera by allowing the surgeon to control the camera using an eye tracking system. The other two or three robotic manipulators carrying surgical instruments are driven via handles in a surgeon console. Since the surgeon has just two hands, operation of the system in procedures utilizing more than two surgical instruments on robotic manipulators requires the surgeon to choose which two instruments s/he will control using the console at any given moment.

In a laparoscopic surgical procedure performed using three manual instruments and a camera, the surgeon manipulates the two primary instruments with his/her right and left hands while a surgical assistant controls the camera and third instrument. Robotic surgery thus gives the surgeon increased control relative to traditional laparoscopy by giving him/her direct control over the camera and third instrument rather than requiring reliance on another person to move those instruments. However, this control lacks the dynamic element of control that occurs in manual laparoscopic procedures where, for example, the surgical assistant moves the camera or third instruments in response to movement of the other instruments or in anticipation of what will next occur with those instruments. Instead, the surgeon must associate the third instrument with a handle of the user input to initiate movement of that instrument or give the system some additional input to cause movement of the camera or third instrument.

This application describes certain modes of operation that enable dynamic, surgeon-controlled movement of a third instrument while the surgeon also controls the two primary instruments.

Although the inventions described herein may be used on a variety of robotic surgical systems, the embodiments will be described with reference to a system of the type shown in FIG. 1. In the illustrated system, a surgeon console 12 has two input devices such as handles 17, 18 that the surgeon selectively assigns to two of the robotic manipulators 14, 15, 16, allowing surgeon control of two of the surgical instruments 10a, 10b, and 10c disposed at the working site at any given time. To control a third one of the instruments disposed at the working site, one of the two handles 17, 18 is operatively disengaged from one of the initial two instruments and then operatively paired with the third instrument. A fourth robotic manipulator, not shown in FIG. 1, supports and maneuvers the laparoscopic camera. The camera may be used by the fourth robotic manipulator using input from an eye tracker 21 disposed at the surgeon console 12.

A control unit 30 is operationally connected to the robotic arms and to the user interface. The control unit receives user input from the input devices corresponding to the desired movement of the surgical instruments, and the robotic arms 14, 15 and 16 are caused to manipulate the surgical instruments accordingly.

DETAILED DESCRIPTION

Figure 1:
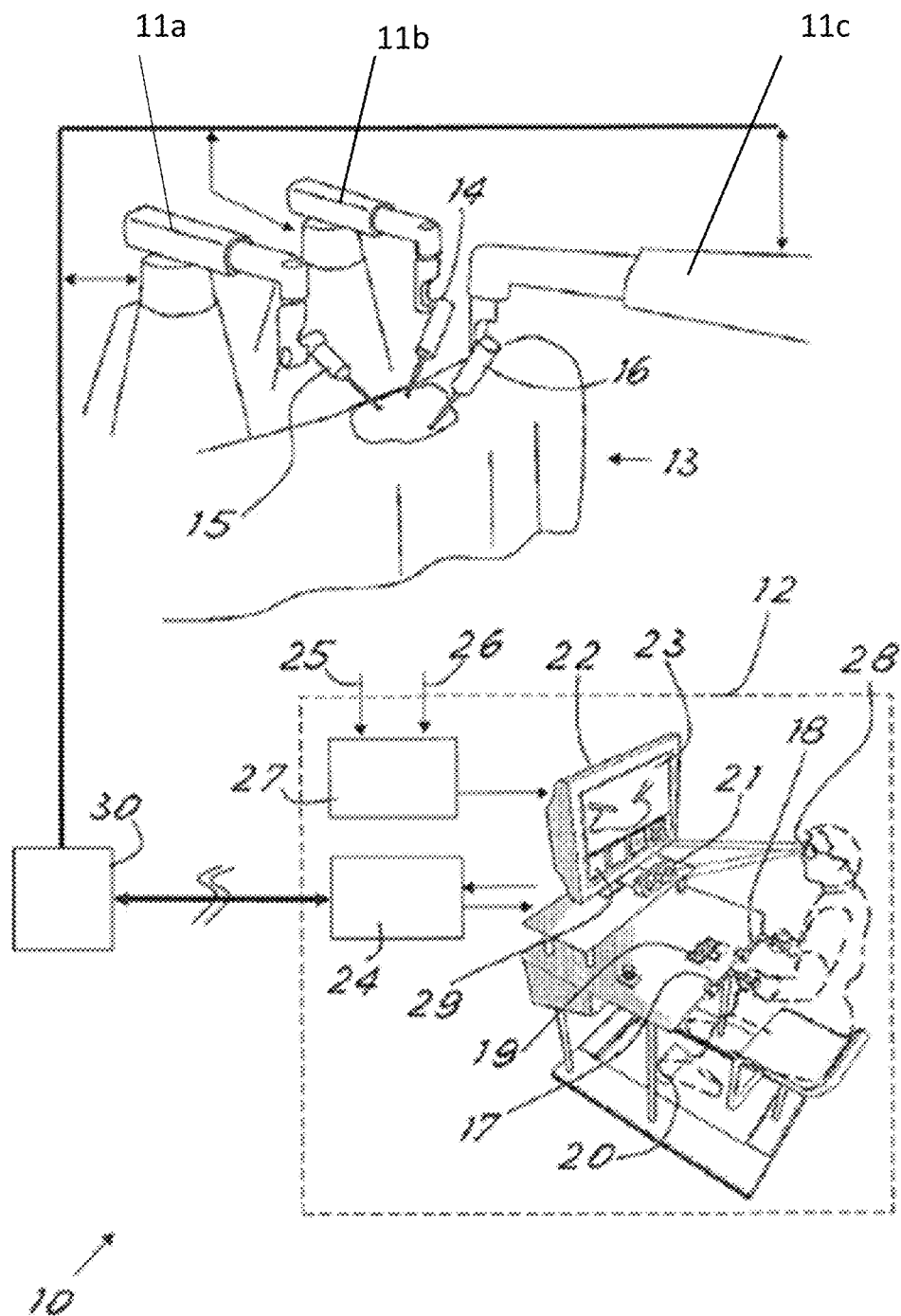
FIG. 1 schematically illustrates elements of a surgical robotic system of a type that may be adapted for use with the disclosed invention.

The purpose of this disclosure is to describe a mode of operation that enables dynamic, system-controlled movement of a fourth robotic manipulator (third instrument, it being assumed that the third manipulator is used to move the camera) while the surgeon controls the movement and operation of the robotic manipulators carrying the two primary instruments. The surgical system may be of a type described in the Background, or any other type of robotic system used to maneuver surgical instruments at an operative site within the body. In some embodiments, the surgical system is one that includes sensors positioned to estimate the forces imparted against each robotically manipulated surgical instrument by tissue or other instruments.

In this description, the terms "primary instruments" or "primary control instruments" will refer to the surgical instruments moveable by robotic manipulators in accordance with the input delivered to the system by the surgeon inputs at the surgeon console. Typically, the surgical instruments under direct control of the user inputs at the surgeon console are the primary instruments. In a practical sense these are the instruments on robotic manipulators that are assigned to corresponding user input devices. Assignment can include assignment using affirmative instrument pairing input by a user, using an eye tracker or alternate input device, or more automated assignment in accordance with an algorithm (e.g. an instrument detection/recognition algorithm resulting in automatic assignment of robotic manipulators to user input devices based on where their corresponding instruments are "seen" by the endoscopic camera in the image view). Primary control instruments may be instruments that move in accordance with the direction, velocity or parameter (or a scaled version of each, according to the scaling factors in use for their operation), or to the location in the body, at/to which the surgeon has deliberately and directly directed them to move using the user input device. Thus primary control instruments include those operatively associated with the user input so they move in the direction and at the rate (or scaled version of either) at which the surgeon is directing them to move using the user input device, even if the system imposes limits on instrument movement such as dynamic rate-slowing as targets are approached, velocity limits, no-fly-zone limits etc.

The term "secondary instrument," "secondary control instrument," or "third instrument" or "dynamically controlled instrument" will refer to an instrument that is also moveable by a robotic manipulator, but whose movement characteristics (e.g. direction, orientation) is based in some way on the characteristics of the directed movement of the one of the primary instruments. In a practical sense this type of instrument is one on a robotic manipulator that has not been uniquely assigned to or paired with a corresponding user input device. While it will be typical for two primary instruments to be used, in some embodiments there might just be one primary instrument. For example, there might just be one primary instrument in a configuration where only one instrument is being controlled by a user input handle because the other user input handle is controlling the camera.

The primary embodiment in this disclosure is a mode of operation where a set of governing laws controls the movement of a third instrument. This mode may be referred to as "Magnet" mode or attraction/repulsion mode because there are times where the third instrument needs to move towards as the two primary instruments and other times where it should move away from the primary instruments. In an attraction mode the dynamically controlled instrument is caused to move, with respect to the primary control instrument, as if it is being magnetically attracted to the primary control instrument. In a repulsion mode the dynamically controlled instrument is caused to move, with respect to the primary control instrument, as if it is being magnetically repulsed by the primary control instrument.

Figure 3:
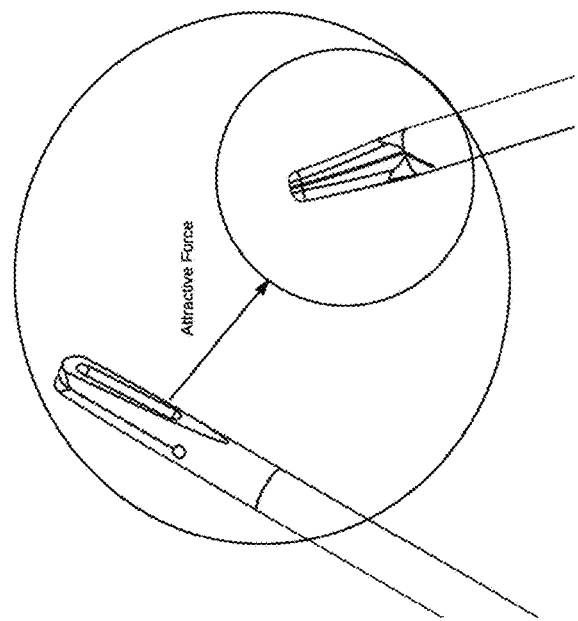
FIG. 3 schematically illustrates the distal ends of two surgical instruments within an operative field with the use of robotically-controlled "attraction" of one the instruments with respect to the other instrument.
Figure 2:
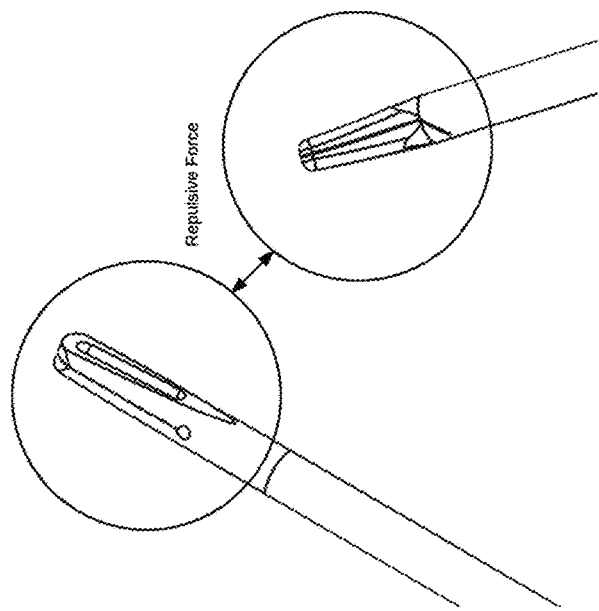
FIG. 2 schematically illustrates the distal ends of two surgical instruments within an operative field with the use of robotically-controlled "repulsion" of one the instruments with respect to the other instrument.

In a "magnet" mode, the third instrument is dynamically controlled so that it will "repulse" away from the primary instruments, as depicted in FIG. 2, when the primary instruments get within a certain distance of one another and such that it will "attract" towards the primary instrument, as depicted in FIG. 3, when the primary instruments are beyond a certain distance. The repulsion or attraction will be a combination of force and position, meaning the vector between the two repulsing or attracting instruments will dictate the amplitude and direction of the applied force to the dynamically controlled instrument. This applied force will be constrained so that it does not put excess force onto tissue and the maximum instrument displacement will be constrained. Maximum displacement may be characterized as the maximum displacement from a first position to a second position, or as the displacement from the primary instrument in a given direction or in any directions. These constraints can prevent movement of the instrument into an area the surgeon does not wish the instrument to enter or unintended collisions with other instruments or tissues.

FIG. 2 schematically illustrates a mode of operation in which the secondary instrument behaves as if there are repulsive forces between the instruments. As an example of repulsion, in cholecystectomy, the third instrument is holding the fundus of the gallbladder during the operation. While the primary instruments are working to remove the gallbladder from the liver bed, the primary instruments are slowly working towards the fundus. As the primary instruments get closer and closer to the fundus, the force applied to the fundus by the third instrument is increased, lifting the gallbladder further. Protections would be in place to stop movement if force or position limits are reached, or when the gallbladder has been completely removed from the liver bed. These events may be detected using input from the systems force/torque sensor, which, in the case of complete separation of the gallbladder, while rapidly decrease.

Additionally, the third instrument would exhibit attraction to the primary instruments when the vector to the primary instruments is beyond a defined threshold. This may be helpful in keeping the instruments within view of the laparoscope or for dynamically controlling the retraction of tissue while in tight spaces. For example, a third instrument shaft could be used to hold up bowel or liver during a procedure. As the primary instruments get closer, the third instrument would repulse away, clearing more space. However, as the primary instruments move away from the third instrument, the third instrument could follow, reducing the tissue retraction and making it easier to find/move to a new desired location, later in the case. FIG. 3 schematically illustrates the mode of operation in which the secondary and, optionally, the primary instrument behaves as if there are attractive forces between them.

Thus, the third instrument could find itself in one of three states: (1) Too close to another instrument and repulsing away (2) Too far away from an instrument and attracting closer or (3) In a goldilocks zone where it is neither too close or too far, so it simply maintains position/force.

The rules governing the repulsion and attraction of the third instrument could be pre-defined and unique to each surgical intervention. The rules could also be adjusted through the surgeon interface. Additionally, surgeon control of the third instrument would still be possible through assigning it to one of the surgeon console handles or through switching to other modes of operations, as described in other disclosures.

The disclosed system thus provides mode of operation that enables the system to control the movement of an instrument that is not under the direct control a user input device, within pre-defined, operative limits. These modes of operation provide a number of advantages, which include:
dynamic control over the "third" (unassigned) in a robotic surgical system
enabling the system to provide dynamic movement of the third instrument while the surgeon maintains control over the primary instruments.

We claim:

1. A surgical robotic system, comprising:
a user interface operable by a user;
at least two surgical instruments;
at least two robotic manipulators on which the at least two surgical instruments are positioned, said robotic manipulators moveable to cause movement of the instruments;
wherein a first one of said robotic manipulators is operatively assigned to the user interface for movement of a first one of the surgical instruments in response to user input signals generated from a user control at the user interface, said first one of the surgical instrument thereby under control as a primary control instrument;
wherein the system is configured to generate dynamic control signals based on a vector defined by the position of the primary control instrument relative to a second one of the surgical instruments operable as a dynamically controlled instrument, and wherein a second one of said robotic manipulators is moveable in response to said dynamic control signals to move the dynamically controlled instrument.

2. The system of claim 1 where the dynamic control signals cause movement of the dynamically controlled instrument based on a vector defined by the position of the primary control instrument to the dynamically controlled instrument.

3. The system of claim 2, where the dynamic control signals cause movement of the dynamically controlled instrument away from the primary control instrument when a distance between the primary control instrument and the dynamically controlled instrument falls below a pre-defined distance, thereby increasing the distance between the primary control instrument and the dynamically controlled instrument.

4. The system of claim 3, wherein the dynamic control signals cause the second robotic manipulator to apply a repulsive force to the dynamically controlled instrument, wherein the repulsive force dynamically adjusts depending on the distance between the primary control instrument and the dynamically controlled instrument.

5. The system of claim 3, wherein the system limits the force and position of the dynamically controlled instrument resulting from the dynamic control signals to within pre-defined or dynamic boundaries.

6. The system of claim 2, where the dynamic control signals cause movement of the dynamically controlled instrument towards the primary control instrument when a distance between the primary control instrument and the dynamically controlled instrument exceeds a pre-defined distance, thereby decreasing the distance between the primary control instrument and the dynamically controlled instrument.

7. The system of claim 6, wherein the dynamic control signals cause the second robotic manipulator to apply an attractive force to the dynamically controlled instrument, wherein the attractive force dynamically adjusts depending on the distance between the primary control instrument and the dynamically controlled instrument.

8. The system of claim 6, wherein the system limits the force and position of the dynamically controlled instrument resulting from the dynamic control signals to within pre-defined or dynamic boundaries.

9. A robot-assisted surgical system comprising:
a user interface operable by a user;
a first robotic manipulator having a first surgical instrument;
a second robotic manipulator having a second surgical instrument;
at least one processor and at least one memory, the at least one memory storing instructions executable by said at least one processor to:
receive user input in response to movement of the input device by a user and cause the manipulator to move the first surgical instrument in response to the user input, determine a vector defined by the position of the first surgical instrument relative to the second surgical instrument, generate dynamic control signals based on the determined vector, and cause the manipulator to move the second surgical instrument in response to said dynamic control signals.

10. The system of claim 9, where the dynamic control signals cause movement of the second instrument away from the first instrument when a distance between the first instrument and the second instrument falls below a pre-defined distance, thereby increasing the distance between the first instrument and the second instrument.

11. The system of claim 10, wherein the dynamic control signals cause the second robotic manipulator to apply a repulsive force to the second instrument, wherein the repulsive force dynamically adjusts depending on the distance between the first instrument and the second instrument.

12. The system of claim 11, wherein the system limits the force and position of the second instrument resulting from the dynamic control signals to within predefined or dynamic boundaries.

13. The system of claim 9, where the dynamic control signals cause movement of the second instrument towards the first instrument when a distance between the first instrument and the second instrument exceeds a pre-defined distance, thereby decreasing the distance between the first instrument and the second instrument.

14. The system of claim 13, wherein the dynamic control signals cause the second robotic manipulator to apply an attractive force to the second instrument, wherein the attractive force dynamically adjusts depending on the distance between the first instrument and the second instrument.

15. The system of claim 13, wherein the system limits the force and position of the second instrument resulting from the dynamic control signals to within predefined or dynamic boundaries.

* * * * *